US00PP16117P2

(12) United States Plant Patent
Boeder

(10) Patent No.: US PP16,117 P2
(45) Date of Patent: Nov. 15, 2005

(54) *CHRYSANTHEMUM* PLANT NAMED 'REDOCK WHITE'

(50) Latin Name: *Chrysanthemum morifolium*
Varietal Denomination: Redock White

(75) Inventor: Mark Roland Boeder, The Hague (NL)

(73) Assignee: Chrysanthemum Breeders Assoc. NV (NL)

( * ) Notice: Subject to any disclaimer, the term of this patent is extended or adjusted under 35 U.S.C. 154(b) by 114 days.

(21) Appl. No.: 10/841,482

(22) Filed: May 10, 2004

(51) Int. Cl.[7] ..... A01H 5/00
(52) U.S. Cl. ..... Plt./294

(58) Field of Search ..... Plt./294

(56) References Cited

PUBLICATIONS

Communication from Community Plant Variety Office Jul. 1, 2005.*
UPOV–ROM Plant Variety Database 2004/04 for *chrysanthemum* plant cultivar redock white.*

* cited by examiner

*Primary Examiner*—Anne Marie Grunberg
*Assistant Examiner*—Annette Para
(74) *Attorney, Agent, or Firm*—Parkhurst & Wendel, L.L.P.

(57) ABSTRACT

A *Chrysanthemum* plant named 'Redock White' characterized by its medium sized single type blooms with white ray-florets and yellow-green disc florets.

3 Drawing Sheets

RELATED CULTIVARS

'Redock White' is related to 'Redock Yellow' (copending U.S. Plant Pat. application), 'Redock Dark' (U.S. Plant Pat. pending), 'Redock Salmon' (U.S. Plant Pat. pending), and 'Redock Orange' (U.S. Plant Pat. pending). These varieties are all mutants of the original 'Redock' (unpatented).

BACKGROUND OF THE INVENTION

'Redock White' is a product of a breeding and selection program which had the objective of finding color mutants of 'Redock'. The new plant of the present invention comprises a new and distinct cultivar of *chrysanthemum* plant that is a natural occurring sport of a parent *chrysanthemum* named 'Redock' (unpatented). A comparison with Parent *chrysanthemum* 'Redock' is also made in this application. The new cultivar was discovered as a whole plant mutation in 2001 by Mark Roland Boeder in a controlled environment (greenhouse) in Rijsenhout Holland. The first act of asexual reproduction of 'Redock White' was accomplished when vegetative cuttings were taken from the initial selection in 2001 in Rijsenhout Holland.

SUMMARY OF THE INVENTION

The present invention is a new and distinct variety of *chrysanthemum* bearing medium sized blooms with white ray-florets and yellow-green disc florets.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
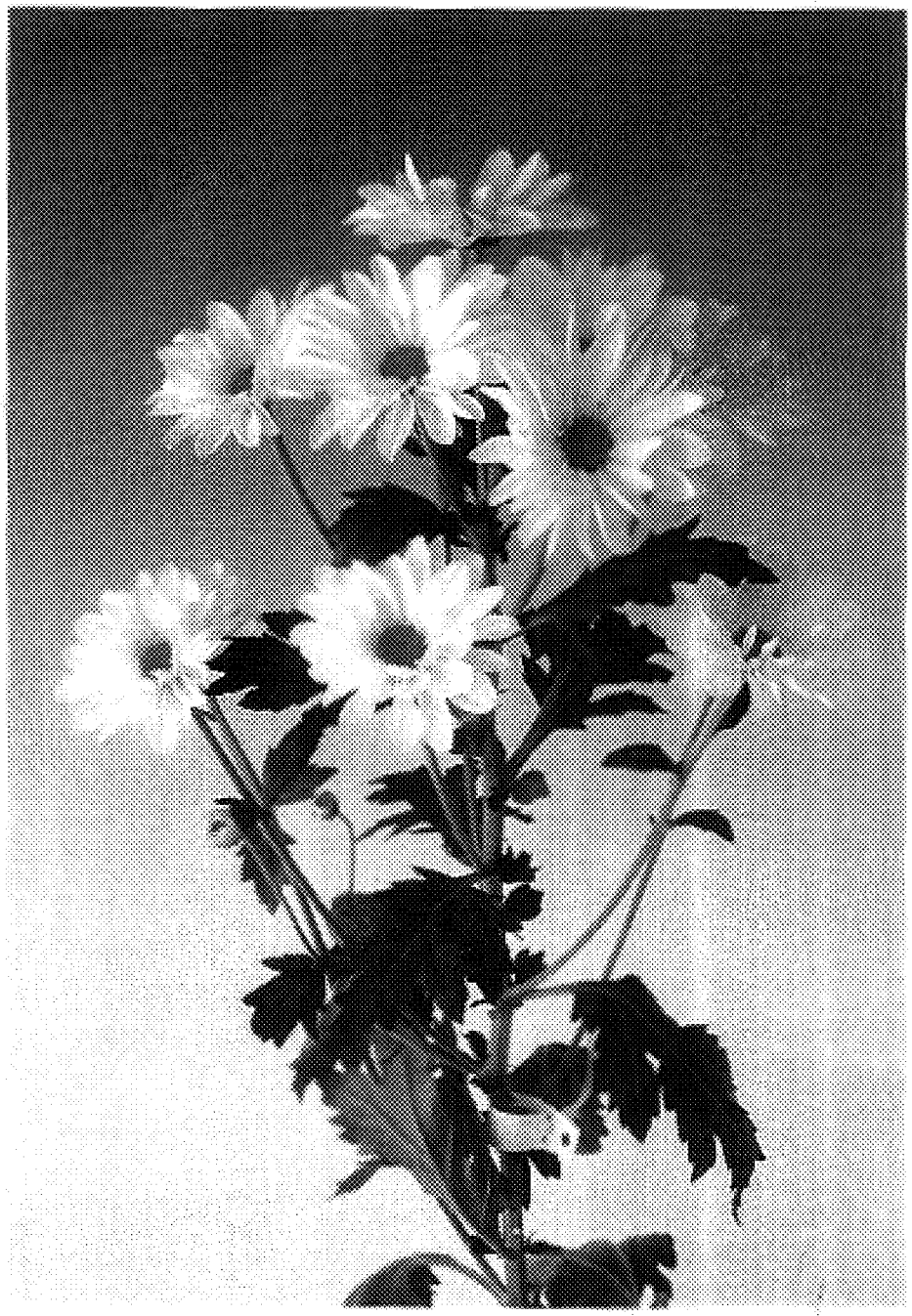
FIG. 1 shows a plant of the cultivar in full bloom.
Figure 2:
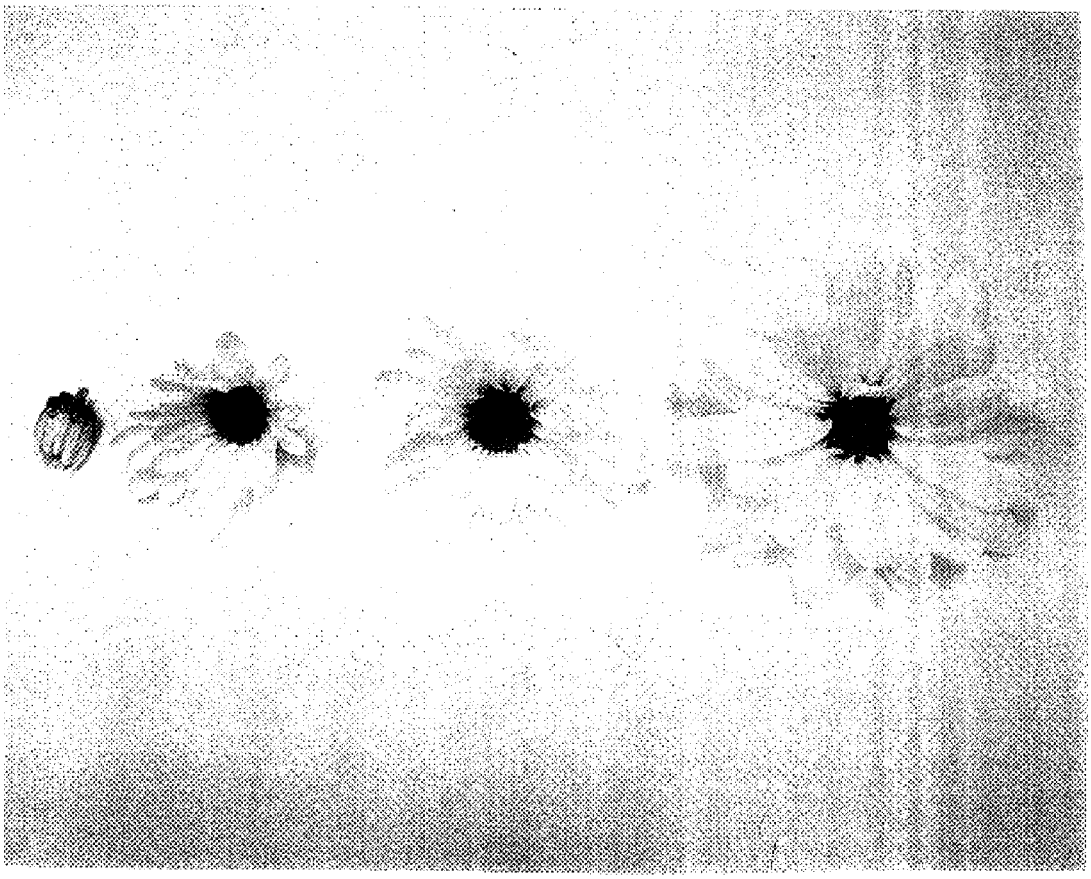
FIG. 2 shows the bloom of the cultivar in various stages.
Figure 3:
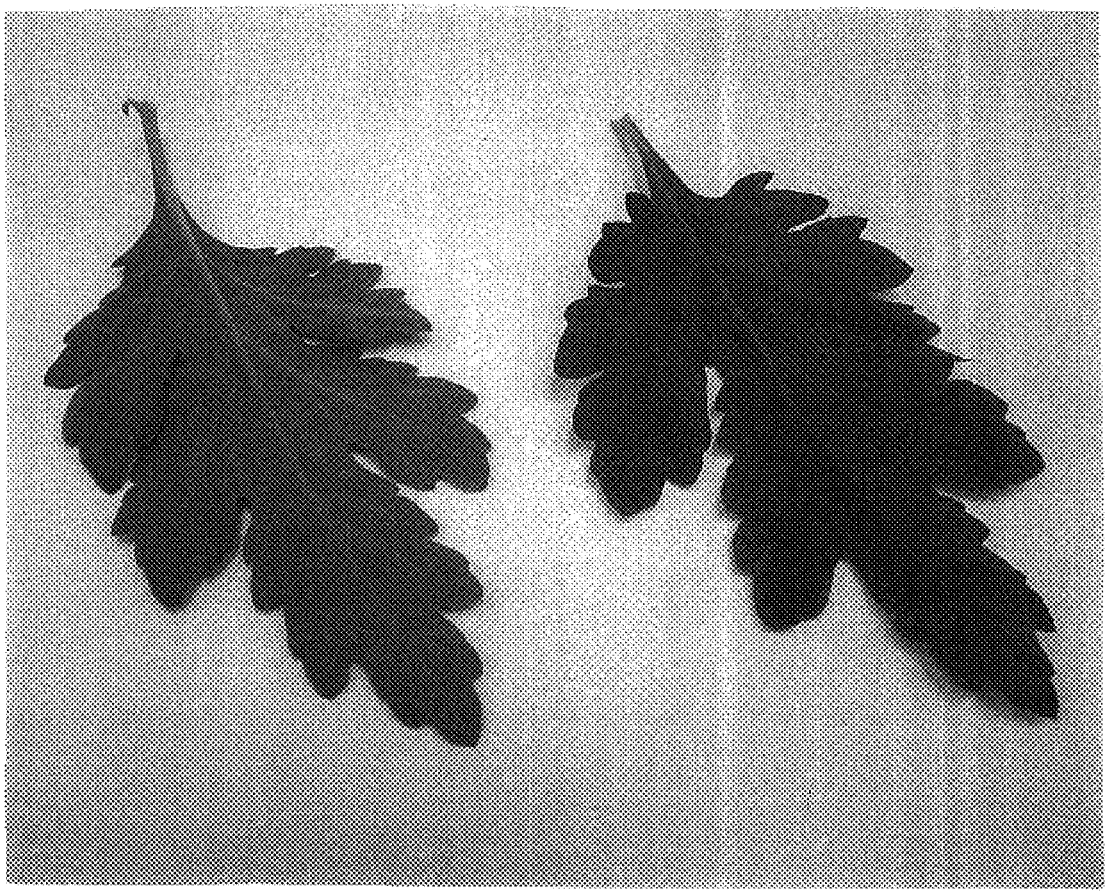
FIG. 3 shows the foliage of the cultivar.

This new variety of *chrysanthemum* is of the botanical classification *Chrysanthemum morifolium* L. The observations and measurements were gathered from plants grown in April/May in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 47 days. After the long day period to flowering growth retardants were applied 3 times in an average dose of 2.5 gram/liter water. No tests were done on disease or insect resistance or susceptibility. This new variety produces medium sized blooms with white ray-florets and yellow-green disc-florets blooming on the plant for 4 weeks. This new variety of *chrysanthemum* has been found to retain its distinctive characteristics throughout successive propagations however the phenotype may vary significantly with variations in environment such as light intensity and temperature. To show the phenotype as described 'Redock White' can be planted without assimilation lightning (high pressure sodium lamps) between week 1 and week 52 under greenhouse conditions in Holland. With assimilation light (minimum level 2500 lux) it can be planted year round under greenhouse conditions in Holland.

The difference between 'Redock' and its sport 'Redock White' is flower color. From the cultivars known to inventor the most similar existing cultivars in comparison to 'Redock White' are the original 'Redock' and its several sports and 'White Reagan' (U.S. Plant Pat. No. 8,784). When 'Redock White' is being compared with 'Redock', the following differences and similarities are noticed: The difference of 'Redock White', and 'Redock' is the (1) ray-floret color. The color of 'Redock White' is white, that of 'Redock' is pink. All other characteristics of members of the 'Redock' family are similar. While when 'Redock White' is being compared with 'Reagan White', the following differences and similarities are noticed. (1) ray-floret color. Both 'Redock White' and 'White Reagan' have white florets. (2) height of bloom. The bloom height of 'Redock White' is high, while that of 'White Reagan' is low. (3) cross-section of ray-florets. This is strongly concave for 'Redock White', while it is flat for 'White Reagan'. (4) vigour. The plants of 'Redock White' are more vigorous than those of 'White Reagan'. (5) plant height. The plants of 'Redock White' are higher than 'White Reagan'.

The following is a description of the plant and characteristics that distinguish 'Redock White' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of CULTIVAR 'Redock White'

| | |
|---|---|
| Bud | |
| Size | Small, cross-section 0.7 cm height 0.9 cm |
| Outside Color | White 155A |
| Involucral bracts | 3 rows, length 8 mm, width 3 mm |
| Involucral bracts among disc-florets | Not present |
| Involucral bracts color | Green 147B |
| Bloom | |
| Type | Single |
| Height | High |
| Size | Medium |
| Fully Expanded | 7.0 cm |
| Number of blooms per single stem | Average of 15–20 |
| Seeds | Not produced |
| Performance (blooming period) | 4 weeks |
| Fragrance | Typical *chrysanthemum* |
| Color | |
| Center of the flower (disc-florets) | Immature yellow-green 144A Mature yellow-green 151C |
| Color of upper surface of the majority of the ray-florets | White 155D |
| Color of the lower surface of the majority of the ray-florets | White 155D |
| Tonality from Distance | A spray mum with white flowers and a yellow-green disc |
| Color of the upper surface of the ray-florets after aging of the plant | White 155D |
| Ray florets | |
| Texture | Upper and under side smooth |
| Number | 26–28 |
| Cross-section | Strongly concave |
| Longitudinal axis of majority | Reflexing |
| Length of corolla tube | Short |
| Ray-floret length | 3.3 cm |
| Ray-floret width | 1.0 cm |
| Ratio length/width | Medium |
| Shape of tip | Pointed, very occasionally round |
| Disc florets | |
| Disc diameter | 0.8–1.0 cm |
| Distribution of disc florets | Numerous, clearly visible at all stages of flowering |
| Shape | Tubular |
| Color | Yellow-green 144A |
| Receptacle shape | Conical raised |
| Reproductive Organs | |
| Stamen (present in disc florets only) | Thin 3 mm in length |
| Stamen color | Yellow-green 144B |

TABLE 1-continued

Botanical Description of CULTIVAR 'Redock White'

| | |
|---|---|
| Pollen | No pollen present |
| Pollen color | Not applicable |
| Styles (present in both ray and disc florets) | Thin |
| Style color | Yellow-green 144B |
| Style Length | 4 mm |
| Stigma color | Yellow-green 144B |
| Stigma Width | 2 mm |
| Ovaries | Enclosed in perianth |
| Plant | |
| Form | A spray mum meant for erect culture |
| Growth habit | Upright |
| Growth rate | Very vigorous |
| Height | 125–135 cm |
| Internodes | 2.5–3.0 cm |
| Spray formation | Corymbiform |
| Stem Color | Yellow-green 147B |
| Stem Strength | Medium |
| Stem Brittleness | Present |
| Stem Anthocyanin Coloration | Absent |
| Peduncle length | Near the top 16 cm, near the middle 23 cm, near the bottom 28 cm |
| Peduncle color | Green 147B |
| Peduncle, attachment | Brittle |
| Peduncle, angle with stem | Small, 30° C. |
| Flowering Response (photo-periodic controlled crop, not natural season) | 47 days |
| Foliage | |
| Color | Upper side yellow-green 147A Under side green 138B |
| Size | large; length 12.0–14.0 cm, width 7.0–8.0 cm |
| Quantity (number per single stem) | 30–34 |
| Shape | Ovate and deeply lobed |
| Texture upper side | Fleshy and glabrous |
| Texture under side | Pubescent |
| Ribs and veins upper side | Ribs and veins well developed |
| Ribs and veins under side | Ribs and veins well developed |
| Venation arrangement | Palmate |
| Shape of the margin | Lobed |
| Shape of Base of Sinus Between Lateral Lobes | Round |
| Margin of Sinus Between Lateral Lobes | Converging |
| Shape of Base | Rounded |
| Apex | Mucronate |
| Petiole length | 2.5 cm |
| Petiole diameter | 4–5 mm |
| Petiole color | Green 147B |

TABLE 2

Differences with the comparison Varieties

| | 'Redock White' | 'Redock' | 'White Reagan' |
|---|---|---|---|
| Ray-floret color | White 155D | Purple 75C | White 155D |
| Bloom height | High | High | Low |
| Cross-section of ray-floret | Strongly concave | Strongly concave | Flat |
| Vigour | Very vigorous | Very vigorous | Vigorous |
| Plant height | 125–135 cm | 125–135 cm | 100–125 cm |

I claim:

1. A new and distinct variety of *chrysanthemum* plant as described and illustrated.

* * * * *